US006922852B1

(12) United States Patent
Blum

(10) Patent No.: US 6,922,852 B1
(45) Date of Patent: Aug. 2, 2005

(54) DISPOSABLE FEMALE URINAL

(76) Inventor: Alvin S. Blum, 2350 Del Mar Pl., Fort Lauderdale, FL (US) 33301

( * ) Notice: Subject to any disclaimer, the term of this patent is extended or adjusted under 35 U.S.C. 154(b) by 39 days.

(21) Appl. No.: 10/971,276

(22) Filed: Oct. 22, 2004

Related U.S. Application Data

(63) Continuation-in-part of application No. 10/663,887, filed on Sep. 16, 2003.

(51) Int. Cl.$^7$ .............................................. A47K 11/00
(52) U.S. Cl. ........................ 4/144.4; 4/144.1; 4/144.2; 604/331
(58) Field of Search ............................. 4/144.1–144.4; 604/327, 329, 331, 322, 317

(56) References Cited

U.S. PATENT DOCUMENTS

| | | | |
|---|---|---|---|
| 2,690,568 A | | 10/1954 | Willis |
| 3,171,136 A | * | 3/1965 | Gibson ........................ 4/144.4 |
| 3,718,431 A | * | 2/1973 | Wild ........................... 4/144.1 |
| 4,023,216 A | | 5/1977 | Li |
| 4,204,526 A | * | 5/1980 | Samuels et al. .............. 600/36 |
| 4,305,161 A | | 12/1981 | Diaz |
| 4,610,675 A | | 9/1986 | Triunfol |
| 5,235,705 A | * | 8/1993 | Belisle ........................ 4/144.3 |
| 5,243,712 A | * | 9/1993 | Cross .......................... 4/144.2 |
| 5,353,805 A | | 10/1994 | Mojena |

FOREIGN PATENT DOCUMENTS

| | | |
|---|---|---|
| GB | 2188545 | 10/1987 |
| JP | 63-191958 | * 8/1988 |

* cited by examiner

Primary Examiner—Khoa D. Huynh
(74) Attorney, Agent, or Firm—Alvin S. Blum

(57) ABSTRACT

A plastic film bag serves as disposable urine collection device especially suitable for female use. The bag has a resealable top opening. Adjacent the top opening along opposed long sides are two tubular members with an end aperture dimensioned for insertion of a finger into each tubular member. When the bag is mounted on two fingers, the fingers can hold the bag open and press the bag against the body on either side of the urinary orifice. In this position, the user can void into the bag without mishap. The device may be used by inserting the bag mounted on the fingers of one hand inside the panties. The device may be formed from a thin plastic film. A grasping tab is connected to the aperture and extends away therefrom adapted to facilitate entrance of the finger into the member. The aperture may be provided with a stiffer annular element to further facilitate insertion of the finger into the tubular member.

13 Claims, 2 Drawing Sheets

DISPOSABLE FEMALE URINAL

This is a continuation in part application of patent application Ser. No. 10/663,887 filed Sep. 16, 2003, incorporated herein by reference.

BACKGROUND OF THE INVENTION

1. Field of the Invention

This invention relates to human waste receptacles, and more particularly to disposable film bags designed for employing two fingers to hold the bag open and sealed around a body orifice for directly receiving waste, especially urine, from a person, especially a female, and for holding it thereafter in sealed form.

2. Description of the Prior Art

BACKGROUND OF THE INVENTION

Women generally discharge body wastes while seated. However, they are reluctant to sit on public toilet seats that may be unclean. When away from a toilet, such as in an automobile, they are also faced with awkward choices not faced by men. U.S. Pat. No. 5,353,805 to Mojena reviews the prior art directed to resolving the problems and discloses a combination bag and tongs for holding the bag opening around the body orifice. U.S. Pat. No. 4,305,161 to Diaz employs a wishbone shaped frame for holding a bag open around the orifice. These inventions rely upon the user to correctly position the opening with a handle remote from the site. Errors in such positioning result in embarrassment and discourage their use.

SUMMARY OF THE INVENTION

It is accordingly an object of the invention to provide a disposable body waste receptacle that is more easily positioned correctly. It is another object that the device be of one piece, easily stored and transported, and completely disposable. It is another object that the device be inexpensive to manufacture. It is yet another object that the device be operated by two fingers to both hold the container open and position the opening properly around the body orifice. The device of the invention is a flexible waterproof bag having opposed long sides and a top opening. A pair of elongate tubular members are affixed to the outside of the bag adjacent the top opening, one on each long side. An aperture is in at least one end of each tubular member and each tubular member is dimensioned to permit entry of a finger therein. For use, a finger is inserted into each tubular member. The two fingers can then hold the bag open. The bag is then positioned so that the body orifice, such as, for example, the urinary meatus, is directly at the opening, with the fingers holding the bag open. The fingers are pressed sealingly against the body on either side of the vulva to reduce leakage. Because the fingers can feel the body structures through the thin wall of the tubular member, correct positioning is more easily achieved and retained during voiding. There is no need to see, nor is there any need for space forward of the body for manipulation as in the prior art devices. The device may be easily used while undergarments are in place by slipping the device mounted on a hand under the panties. The bag is provided with a sealing system, such as the rib and groove well known in food bags, affixed to the inner surface of the bag adjacent the top opening. After filling, the contents are sealed by pressing the outer surface of the two long sides together. There is no need to soil the hands by reaching into the bag to seal. The device is made of a waterproof material such as, for example but not limited to, wax paper or plastic film so as to be inexpensive to manufacture. Each aperture may be reinforced with an annular element to hold the tubular member open for more easily slipping the finger into the member. Each aperture is supplied with a grasping tab connected to the aperture and extending away from the tubular member. By grasping the tab with the fingers of the other hand, the aperture may be held open and the finger may be more easily slipped into the member. When the device is fabricated of a flaccid, thin, plastic film such as polyolefin, the tab will enable the user to hold the end of the member steady while the finger is being inserted.

Although this invention is primarily directed to female urination, it will also find application for male use, and for defecation as well as urination. These and other objects, features, and advantages of the invention will become more apparent when the detailed description is studied in conjunction with the drawings in which like elements are designated by like reference characters in the various drawing figures.

BRIEF DESCRIPTION OF THE DRAWINGS

FIG. 3 is a perspective view of the device partially open.

FIG. 4 is a sectional view taken through line 4—4 of FIG. 3 with the device in use.

DETAILED DESCRIPTION OF PREFERRED EMBODIMENTS

Figure 1:
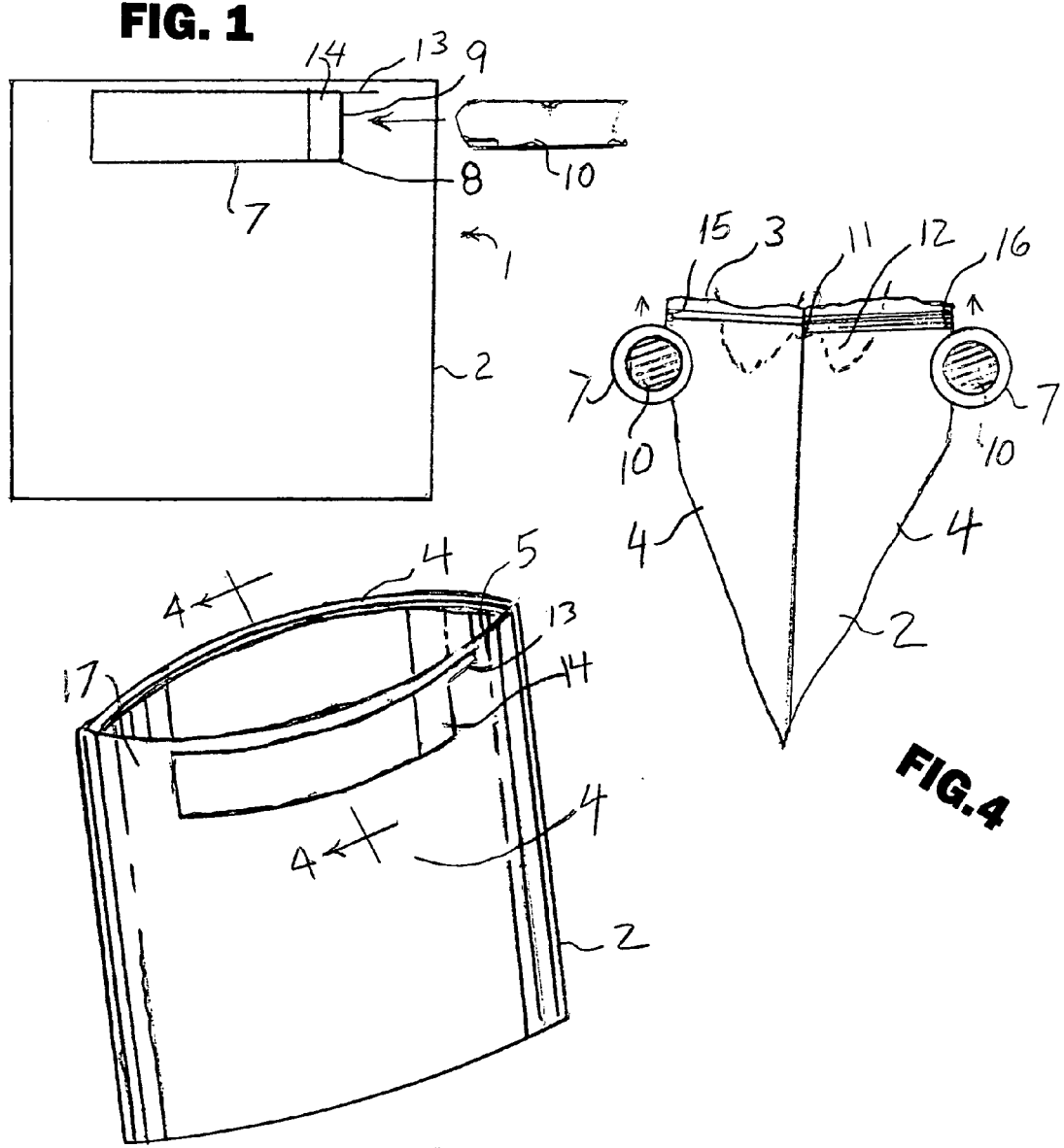
FIG. 1 is a front elevation view of a device of the invention.
Figure 2:
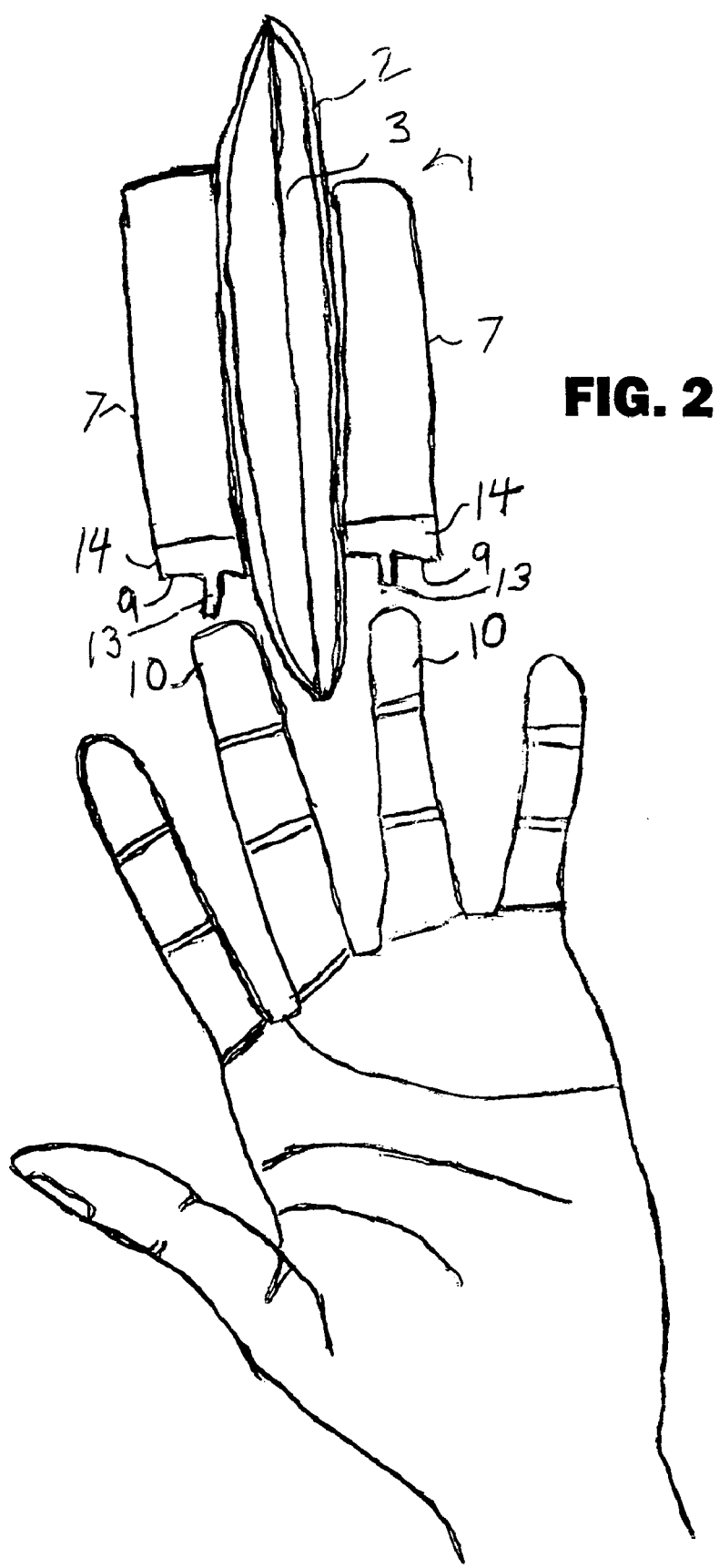
FIG. 2 is a top view of the device partially open, with fingers about to be inserted into the tubular members.

Referring now to the drawing FIGS. 1–4, a waterproof, self-contained disposable device 1 of the invention is constructed for mounting on two fingers 10 of one hand or one finger from each hand, as desired. The device includes a bag 2 having a top opening 3, and opposed long sides 4. In a preferred form, the inner aspect 6 of the bag adjacent the top opening is provided with a sealing means 5 such as, for example, but not limited to, a rib 15 and an opposed groove 16 for sealing the contents after use. Affixed on the outside 17 of the bag, adjacent the top opening, a tubular member 7 extends along each long side 4. An aperture 9 is provided on at least one end 8 of each tubular member. The aperture and member are dimensioned for easy insertion of a finger therein. A tab 13 of any shape that enables it to be grasped by two fingers is connected to the aperture and extend away from the aperture to facilitate sliding the finger into the member. By grasping the tab, the aperture will be held steady as the finger slides through the aperture and into the tubular member. Optionally, an annular element 14 may be provided at the aperture to hold it open to further facilitate mounting the device on the fingers. The annular element may take the form of a strip of stiffer plastic when the rest of the device is made from a thin, flaccid material such as a polyethylene film, for example.

As best seen in FIG. 4, the device, when mounted on two fingers, is easily positioned with the open top of the bag around the urinary orifice 11. Each finger 10 and tubular member 7 is easily held against the body on either side of the vulva 12. This position is easily maintained during voiding by sense of touch, so that the area need not be exposed. The device may even be inserted and held in place with one hand inserted under the undergarment. After use, the bag is removed from the fingers, then the top is sealed, and it discarded when convenient. If desired, a tissue may be provided with each bag.

While I have shown and described the preferred embodiments of my invention, it will be understood that the invention may be embodied otherwise than as herein specifically illustrated or described, and that certain changes in form and arrangement of parts and the specific manner of practicing the invention may be made within the underlying idea or principles of the invention.

What is claimed is:

1. A one-piece, self contained disposable device for mounting on two fingers for directly receiving waste from a person's body orifice, the device comprising:
   a) a waterproof bag having a top opening, a closed bottom, and opposed long sides;
   b) sealing means encircling an inner aspect of the bag adjacent the top opening;
   c) a pair of tubular members affixed to the outside of the bag, each member extending along the long side adjacent the top opening, each member provided with an aperture on at least one end, each aperture and member dimensioned for receiving a finger therein such that the fingers may hold open the top opening while positioning the fingers and the bag around the orifice; and
   d) each member having a grasping tab connected to and protruding outwardly from the aperture said grasping tab adapted to facilitate entrance of the finger into the member.

2. The device according to claim 1 constructed of plastic film.

3. The device according to claim 1 in which the sealing means is a rib and groove mechanism.

4. The device according to claim 3 wherein each member further comprising an annular element at the aperture constructed to hold the aperture open to facilitate insertion of a finger therein.

5. The device according to claim 1 in which the body orifice is the urinary meatus and the waste is urine.

6. The device according to claim 1 wherein each member further comprising an annular element at the aperture constructed to hold the aperture open to facilitate insertion of a finger therein.

7. A one-piece, self contained disposable device for mounting on two fingers for directly receiving urine from a female person's urinary orifice, the device comprising:
   a) a waterproof bag having a top opening, a closed bottom, and opposed long sides;
   b) sealing means on an inner aspect of the bag adjacent the top opening;
   c) a pair of tubular members affixed to the outside of the bag, each member extending along the long side adjacent the top opening, each tubular member provided with an aperture on at least one end, each aperture and tubular member dimensioned for receiving a finger therein such that the fingers may hold open the top opening while positioning the fingers and the bag around the orifice; and
   d) each member having a grasping tab connected to and protruding outwardly from the aperture said grasping tab adapted to facilitate entrance of the finger into the member.

8. The device according to claim 7 constructed of flaccid plastic film.

9. The device according to claim 8 in which the sealing means is a rib and groove mechanism.

10. The device according to claim 7 in which the sealing means is a rib and groove mechanism.

11. The device according to claim 10 wherein each member further comprising an annular element at the aperture constructed to hold the aperture open to facilitate insertion of a finger therein.

12. The device according to claim 7 wherein each member further comprising an annular element at the aperture constructed to hold the aperture open to facilitate insertion of a finger therein.

13. A one-piece, self contained disposable device for mounting on two fingers for directly receiving urine from a female person's urinary orifice, the device comprising:
   a) a waterproof bag having a top opening, a closed bottom, and opposed long sides;
   b) sealing means on an inner aspect of the bag adjacent the top opening;
   c) a pair of tubular members affixed to the outside of the bag, each extending along the long side adjacent the top opening, each tubular member provided with an aperture on at least one end, each aperture and tubular member dimensioned for receiving a finger therein such that the fingers may hold open the top opening while positioning the fingers and the bag around the orifice and against a body part;
   d) each member having an annular element encircling the aperture to hold it open to facilitate insertion of the finger therein; and
   e) each member having a grasping tab connected to and protruding outwardly from the aperture said grasping tab adapted to facilitate entrance of the finger into the member.

* * * * *